(12) United States Patent
Loginova et al.

(10) Patent No.: US 8,349,338 B2
(45) Date of Patent: *Jan. 8, 2013

(54) COSMETIC PRODUCT CONTAINING ACRYLATES

(75) Inventors: Yelena Loginova, Bronx, NY (US); Domnica Cernasov, Ringwood, NJ (US); Ralph Macchio, Sparta, NJ (US)

(73) Assignee: Coty B.V., Haarlem (NL)

( * ) Notice: Subject to any disclaimer, the term of this patent is extended or adjusted under 35 U.S.C. 154(b) by 0 days.

This patent is subject to a terminal disclaimer.

(21) Appl. No.: 09/975,756

(22) Filed: Oct. 10, 2001

(65) Prior Publication Data

US 2003/0049285 A1     Mar. 13, 2003

(30) Foreign Application Priority Data

Jul. 24, 2001    (DE) .................................. 101 36 882

(51) Int. Cl.
*A61K 8/02* (2006.01)

(52) U.S. Cl. ...................................................... 424/401

(58) Field of Classification Search ............... 424/70.31, 424/401, 400, 70.16; 514/944
See application file for complete search history.

(56) References Cited

U.S. PATENT DOCUMENTS

| | | | |
|---|---|---|---|
| 3,639,572 A | | 2/1972 | Heinrich et al. |
| 4,423,031 A | | 12/1983 | Murui et al. |
| 5,653,969 A | * | 8/1997 | Carballada et al. ........ 424/70.16 |
| 5,804,173 A | * | 9/1998 | Hutchins et al. ........... 424/70.16 |
| 5,925,337 A | | 7/1999 | Arraudeau et al. ............. 424/63 |
| 6,190,647 B1 | * | 2/2001 | Karlen et al. ................ 424/70.2 |
| 6,524,565 B1 | * | 2/2003 | Loginova ..................... 424/70.7 |
| 6,524,596 B1 | * | 2/2003 | Samain et al. ................ 424/401 |
| 2002/0035161 A1 | | 3/2002 | Segura et al. |
| 2006/0159638 A1 | | 7/2006 | Segura et al. |

FOREIGN PATENT DOCUMENTS

| | | |
|---|---|---|
| EP | 0590604 A2 | 4/1994 |
| FR | 2787322 A1 | 6/2000 |
| JP | 54-151139 A | 11/1979 |

OTHER PUBLICATIONS

"European Application Serial No. EP0200267, European Search Report dated Sep. 22, 2004", 2 pgs.

* cited by examiner

*Primary Examiner* — San-Ming Hui
(74) *Attorney, Agent, or Firm* — Schwegman Lundberg & Woessner, P.A.

(57) ABSTRACT

The invention refers to a cosmetic gel product containing acrylates and to a method for manufacturing the said product. The gel comprises 0.01-80% by weight of a film-forming agent on the basis of an acrylate copolymer or acrylate derivate which agent is emulsifiable with water, 0.01-90% by weight of an aliphatic hydrocarbon solvent or a volatile silicone derivate, both of which are not miscible with water and are emulsifiable with water-based ingredients and/or with ingredients on the basis of organic solvents in the presence of an emulsifier.

24 Claims, No Drawings

COSMETIC PRODUCT CONTAINING ACRYLATES

RELATED APPLICATIONS

This application claims priority to German Patent Application No. 101 36 882.8, filed Jul. 24, 2001.

BACKGROUND OF THE INVENTION

From U.S. Pat. No. 5,925,337, a waterproof mascara composition is known which contains 2-40% by weight of a wax, 5-15% by weight of a thickening agent, 35-50% by weight of a volatile organic solvent and 1-35% by weight of a water-soluble film-forming agent, wherein the last-named agent may e.g. also be an acrylate polymer. The composition does not contain any emulsifier.

SUMMARY OF THE INVENTION

In its product aspect, the present invention includes a cosmetic gel. The cosmetic gel includes a film-forming agent comprising an acrylate copolymer or an acrylate derivate, wherein the film-forming agent is emulsifiable with water. The gel also includes an aliphatic hydrocarbon solvent and, optionally, a volatile silicone derivate wherein the aliphatic hydrocarbon solvent and, optionally, volatile silicone derivates are not miscible with water and are emulsifiable with one or more water-based ingredients. The ingredients are selected on a basis of organic solvents in the presence of an emulsifier. The gel also includes a non-ionic emulsifier and water.

In another embodiment, the present invention includes a cosmetic gel that includes a film forming agent. The film forming agent includes an acrylate derivate and the film forming agent is emulsifiable with water. The cosmetic gel also includes an aliphatic hydrocarbon solvent and, optionally, a volatile silicone derivate wherein the aliphatic hydrocarbon solvent and volatile silicone derivate are not miscible with water and are emulsifiable with one or more water-based ingredients. The cosmetic gel also includes a non-ionic emulsifier and water.

In its product aspect, the present invention includes a method for manufacturing a cosmetic gel. The method includes providing a mixture. The mixture includes a film-forming agent comprising an acrylate copolymer and, optionally, acrylate derivate, water and a non-ionic emulsifier. The mixture is heated to a temperature in the range of 45 to 50 degrees Centigrade to form an emulsion. The emulsion is mixed with a volatile aliphatic hydrocarbon solvent and, optionally, a volatile silicone derivate. Neither of the hydrocarbon solvent nor the volatile silicone derivate are miscible with water. Both the hydrocarbon solvent and silicone derivate are emulsifiable with water-based ingredients and/or with ingredients on the basis of organic solvents in the presence of an emulsifier.

The emulsion is homogenized at 1500 to 3000 rpm for 15 to 60 minutes to form a two-phase liquid system, wherein water is completely distributed in the aqueous phase in the form of micro-droplets. The two-phase liquid system mixture is cooled to 25-30 degrees Centigrade, while mixing at a rate of 100 to 600 rpm.

In one other embodiment, the present invention includes a cosmetic made with the cosmetic gel.

DETAILED DESCRIPTION

The present invention provides a new cosmetic intermediate which, due to its special structure, is suitable for forming a soft and elastic product with waterproof characteristics and which can be processed into further cosmetic products adding both water-based ingredients and ingredients on the basis of organic solvents.

According to the invention, the cosmetic composition containing acrylates is characterized in that it contains (a) 0.01-80% by weight of a film-forming agent on the basis of an acrylate copolymer or acrylate derivate which agent is emulsifiable with water;

(b) 0.01-90% by weight of an aliphatic hydrocarbon solvent or a volatile silicone derivate both of which are not miscible with water and are emulsifiable with water-based ingredients and/or with ingredients on the basis of organic solvents in the presence of an emulsifier;

(c) 0.01-5% by weight of a non-ionic emulsifier;

(d) 1.00-80% by weight of water; and wherein the composition has the structure of a gel.

Advantageously, alkoxylated alcohols, ethoxylated alcohols, polyglyceryl esters and mixtures thereof can be used as emulsifiers. The said substances are non-ionic emulsifiers which contain e.g. a polyol group, a polyalkylglycol ether group or a combination thereof, such as e.g. addition products of 2-30 mole ethylene oxide TO LINEAR fatty alcohols having 8-22 carbon atoms and to fatty acids having 12-22 carbon atoms, as hydrophylic group. The said substances further include polyglycerine esters, such as e.g. polyglycerine ricinoleate or polyglycerine poly-12-hydroxystearate, and mixtures of these different substance classes.

A preferred emulsifier is, for example, Laureth-20, Laureth-23, Oleth-20, Steareth-20, Steareth-50, Ceteareth-20, Ceteareth-30.

An ethyl acrylate/methyl methacrylate copolymer can be used as acrylate copolymer, for example.

It is particularly preferred that the film-forming agent be an ethyl acrylate/methyl methacrylate copolymer in which the ratio of ethyl acrylate units to methyl methacrylate units in the polymer is in the range of 7.5-8.5:1.8-2.3.

Acrylic acid, methacrylic acid or their esters also can be used (herein called "acrylate derivates").

A preferred range for the acrylate copolymer or acrylate derivate is between 0.1 and 50% by weight, particularly 0.1-15% by weight.

Isoparaffins e.g. isododecane, pentane, hexane, decane etc. are preferably used as aliphatic hydrocarbon solvent which is not miscible with water. Isododecane is special preferred.

A preferred range for the aliphatic hydrocarbon solvent or the volatile silicone derivate is between 30 and 75% by weight, particularly in the range of 51-70% by weight.

Advantageously, a compound such as Dimethicone or Cyclomethicone can be used as volatile silicone derivate.

A preferred silicone derivate is e.g. decamethylcyclopentasiloxysiloxane (Silicone SS4230).

The preferred water content is in the range of 1.0 to 40% by weight, particularly 1.0 to 20% by weight.

The product according to the invention is a gel which is particularly characterized in that a combination of solvent and film-forming agent is obtained which is stable in the cosmetic formulation. Such a stable combination having the characteristics of a gel was surprising for those skilled in the art, and it permits the manufacture of cosmetic products which are particularly elastic and soft. For example, in the case of an ethyl acrylate/methyl methacrylate copolymer, the elasticity can be increased 4- to 5-fold compared to the elasticity of the film-forming agent used.

The elasticity was determined using the strip test method, which is carried out as follows:

The measurement of length of an elastic film made from a polymer has been carried out. Two separate films A and B of about 6.0 mil thick have been poured on the non-sticky surface with a Bird applicator. Film A includes an aqueous acrylate copolymer (Acrylates Copolymer: Water about 50:50, emulsifier), and film B includes 50% components of film A and 50% isododecane. In 24 hours, at 25° C. the specimens were prepared by cutting the strips of about 50×25 mm. One end of each of the strip was attached to a ruler. The specimen has been tested by stretching the strip without breaking in the direction of the end of the ruler. The result for film A was 101 mm, for film B 406 mm.

The softness of the composition after applying it to the skin or to an even surface is also considerably higher than that of the original film-forming agent. This improves the feeling, which plays a central role in the selection of a product by the user.

The invention also refers to the manufacture of a cosmetic composition containing acrylates. The method consists in that
a) a mixture of 0.1-80% by weight of a film-forming agent on the basis of an acrylate copolymer or acrylate derivate, 1.0-80% by weight of water and 0.01-1% by weight of a non-ionic emulsifier is heated up to a temperature in the range of 45-50° C.;
b) at this temperature the obtained emulsion is mixed with 0.1-90% by weight of a volatile aliphatic hydrocarbon solvent or a volatile silicone derivate, wherein the solvent or the silicone derivate are not miscible with water, but are emulsifiable with water-based ingredients and/or with ingredients on the basis of organic solvents in the presence of an emulsifier, and wherein a two-phase liquid system is obtained after homogenization at 1500-3000 rpm during 15-60 min until the organic phase which is not miscible with water is completely distributed in the aqueous phase in the form of micro-droplets; and
c) the mixture is cooled down to 25-30° C. at a rate of 300 to 600 rpm until a homogeneous gel is obtained.

The emulsion of stage a) may contain further cosmetic constituents, such as esters, oils, sun-blocking agents, perfume, preservatives, vitamins, scavengers and other auxiliary and/or active cosmetic substances. The said substances, if any, can be manufactured as separate phase and added to the emulsion of stage a).

The method according to the invention is characterized by a strictly defined sequence of steps and an unusual temperature regime. It is only in this way that a stable formulation having the above-mentioned advantages can successfully be obtained.

The invention will hereinafter be explained more precisely by means of examples which, however, do not constitute any limitation of the invention. All quantities are given in per cent by weight.

| Example 1 | Basic Gel |
|---|---|
| Ethyl acrylate/methyl methacrylate | 24.5 |
| Water | 25.0 |
| Laureth-20 | 0.3 |
| sododecane | 50.0 |

The copolymer is mixed with water and the emulsifier Laureth-20, and the mixture is heated up to 45° C. Isododecane is added, and the temperature is increased to 50° C. while stirring. After that, homogenization takes place at 2200 rpm for a time of 18 minutes in a laboratory vessel of 1000 ml volume. Subsequently, the mixture is cooled down to 27° C. and stirred at a rate of 400 rpm for approx. 5 min.

| Example 2 | Sun-blocking Gel |
|---|---|
| Basic gel of Example | 198 |
| Octyl methoxycinnamate | 2 |

The processing is done as in Example 1 mixing the sun-blocking agent with the copolymer, water and the emulsifier.

| Example 3 | Gel Lotion |
|---|---|
| Basic gel of Example 1 | 80 |
| Oil or ester | 20 |

The processing is done as in Example 2.

The invention claimed is:

1. A cosmetic gel comprising:
a film-forming agent selected from the group comprising one or more ethyl acrylate/methylmethacrylate copolymers in which the ratio of ethyl acrylate units to methyl methacrylate units in the polymer is in the range of 7.5-8.5:1.8-2.3, wherein the film-forming agent is emulsifiable with water;
a solvent selected from the group consisting of an aliphatic hydrocarbon or a volatile silicone derivate or combinations thereof wherein the aliphatic hydrocarbon solvent and volatile silicone derivate solvent are not miscible with water and are emulsifiable with the film-forming agent;
a non-ionic emulsifier; and
water;
wherein the gel has an elasticity that is 4 to 5 times greater than the elasticity of the film-forming agent alone and the gel has a softness greater than the film-forming agent.

2. A cosmetic gel, comprising:
a film-forming agent comprising one or more ethyl acrylate/methylmethacrylate copolymers, wherein the film-forming agent is emulsifiable with water;
a solvent selected from the group consisting of aliphatic hydrocarbon solvent and a volatile silicone derivate wherein the aliphatic hydrocarbon solvent and volatile silicone derivate are not miscible with water and are emulsifiable with one or more water-based ingredients;
a non-ionic emulsifier; and
water;
wherein the gel has an elasticity that is 4 to 5 times greater than the elasticity of the film- forming agent alone and the gel has a softness greater than the film-forming agent.

3. The cosmetic gel according to claim 2 wherein the emulsifier is chosen from the group consisting of alkoxylated alcohols, ethoxylated alcohols, polyglyceryl esters and mixtures thereof.

4. The cosmetic gel according to claim 1 wherein it additionally contains auxiliary cosmetic substances, active cosmetic substances or mixtures thereof.

5. The cosmetic gel of claim 1 wherein the aliphatic hydrocarbon solvent has a concentration of 0.01 to 90 percent by weight of the gel.

6. The cosmetic gel of claim 1 wherein the volatile silicone derivate has a concentration of 0.01 to 90 percent by weight of the gel.

7. The cosmetic gel of claim 2 wherein the non-ionic emulsifier has a concentration of 0.01 to 5 percent by weight of the gel.

8. The cosmetic gel of claim 2 wherein the water has a concentration of 1.00 to 80 percent of the gel.

9. The cosmetic gel of claim 1 wherein the aliphatic hydrocarbon solvent is selected from one or more of isododecane, pentane, hexane, decane, or other isoparaffin.

10. The cosmetic gel of claim 1 wherein the aliphatic hydrocarbon solvent or volatile silicone derivate ranges from 30 to 75% by weight.

11. The cosmetic gel of claim 1 wherein the volatile silicone derivate is selected from one or more of dimethicone, cyclomethicone, or decamethylcyclopentasiloxysiloxane.

12. The emulsifier of claim 3 selected from one or more of Laureth-20, Laureth-23, Oleth-20, Steareth-20, Steareth-50, Ceteareth-20, and Ceteareth-30.

13. A cosmetic made with the gel of claim 1.

14. An emulsion comprising:
a mixture of a film-forming agent comprising one or more of ethyl acrylate/methyl methacrylate copolymer in which the ratio of ethyl acrylate units to methyl methacrylate units in the copolymer is in the range of 7.5-8.5: 1.8-2.3;
water; and
a non-ionic emulsifier;
wherein the gel has an elasticity that is 4 to 5 times greater than the elasticity of the film-forming agent alone and the gel has a softness greater than the film-forming agent.

15. The emulsion of claim 14, further comprising an aliphatic hydrocarbon solvent wherein the aliphatic hydrocarbon is not miscible in water but is emulsifiable with the emulsion.

16. The emulsion of claim 14, further comprising a volatile silicone derivate wherein the volatile silicone derivate is not miscible in water but is emulsifiable with the emulsion.

17. A gel comprising the emulsion of claim 14 wherein the gel has an elasticity that is 4 to 5 times greater than the elasticity of the film-forming agent alone and the gel has a softness greater than the film-forming agent.

18. A cosmetic comprising the gel of claim 17.

19. A sun-blocking cosmetic comprising the gel of claim 17 and a sun blocking agent.

20. A lotion comprising the gel of claim 17 and an oil.

21. The cosmetic gel of claim 1, wherein the amount of the film-forming agent in the gel is in the range of between 0.1 and 15% by weight of the gel and the amount of the solvent is in the range of between 51 and 70% by weight of the gel.

22. The cosmetic gel of claim 2, wherein the amount of the film-forming agent in the gel is in the range of between 0.1 and 15% by weight of the gel and the amount of the solvent is in the range of between 51 and 70% by weight of the gel.

23. The cosmetic gel of claim 15, wherein the amount of the film-forming agent in the emulsion is in the range of between 0.1 and 15% by weight of the emulsion and the amount of the aliphatic hydrocarbon solvent is in the range of between 51 and 70% by weight of the emulsion.

24. The cosmetic gel of claim 16, wherein the amount of the film-forming agent in the emulsion is in the range of between 0.1 and 15% by weight of the emulsion and the amount of the volatile silicone derivate is in the range of between 51 and 70% by weight of the emulsion.

* * * * *

UNITED STATES PATENT AND TRADEMARK OFFICE
CERTIFICATE OF CORRECTION

| | | |
|---|---|---|
| PATENT NO. | : 8,349,338 B2 | Page 1 of 1 |
| APPLICATION NO. | : 09/975756 | |
| DATED | : January 8, 2013 | |
| INVENTOR(S) | : Loginova et al. | |

It is certified that error appears in the above-identified patent and that said Letters Patent is hereby corrected as shown below:

On the title page, in column 2, under "Other Publications", line 2, delete "dated" and insert --mailed--, therefor In the Claims Column 4, line 55, in claim 2, delete "film- forming" and insert --film-forming--, therefor Signed and Sealed this
Second Day of December, 2014

Michelle K. Lee
*Deputy Director of the United States Patent and Trademark Office*